United States Patent [19]

Fruehwirth

[11] Patent Number: Plant 7,234

[45] Date of Patent: May 22, 1990

[54] POINSETTIA PLANT '135'

[75] Inventor: Franz Fruehwirth, Encinitas, Calif.

[73] Assignee: Paul Ecke Ranch, Inc., Encinitas, Calif.

[21] Appl. No.: 263,494

[22] Filed: Oct. 27, 1988

[51] Int. Cl.[5] ..... A01H 5/00

[52] U.S. Cl. ..... Plt./86

[58] Field of Search ..... Plt./86

*Primary Examiner*—James R. Feyrer

*Attorney, Agent, or Firm*—Arnold, White & Durkee

[57] ABSTRACT

The present disclosure describes a new Poinsettia cultivar, named '135', having attractive bicolored red and white flower bracts. '135' is stiff-stemmed with vigorous growth habits and self-branching traits which increases its value as a flowering branched plant. This new poinsettia cultivar originated as a sport of the cultivar described in U.S. Plant No. 3,889.

1 Drawing Sheet

BACKGROUND OF THE INVENTION

Poinsettia '135' is a stiff-stemmed, vigorous poinsettia with attractive bicolored red and white flower bracts. White is the predominant color with red splotches of various sizes and shapes randomly scattered over the bracts. The plant has self-branching traits which increases its value as a flowering branched plant.

This new poinsettia cultivar originated as a sport of the cultivar of U.S. Plant No. 3,889 in a greenhouse in Encinitas, Calif. It was selected because of the unique coloration which distinguishes it from other poinsettia cultivars, and making it a desirable plant for commercial greenhouse production. It is a more vigorous plant and branches more freely than the cultivar of U.S. Plant No. 3,889. The bract color is red on white in contrast to the pink on red colors of the cultivars of U.S. Plant Nos. 3,889 or 4,860. The bracts are more erect and do not droop like that of U.S. Plant No. 4,860, giving it a lively and fresh appearance. After selection, vegetatively reproduction of this plant by stem cuttings for test purposes in Encinitas, Calif., and clones of the plant were subjected to successive generations of vegetative propagation. The bract colors and the percentage of each color of the flower bracts remain stable from generation to generation.

DESCRIPTION OF THE PHOTOGRAPHS

Poinsettia '135' is illustrated in the accompanying color photographs. The upper photo is a side view of a branched plant in full flower. The lower photo is a top view of a plant showing flower and bract formation.

DESCRIPTION OF THE PLANT

The following is a detailed description of this new poinsettia as observed in a greenhouse in Encinitas, Calif., during December, 1987. Recorded observations from flowering plants, grown as 3 unpinched plants per pot were observed. The pot was 14 cm. in diameter and 11 cm. in height. Color designations were compared to the 1986 edition of R.H.S. Colour Chart, first published in 1966 by The Royal Horticultural Society, London, England.

THE PLANT

Origin: Sport of the cultivar of U.S. Plant No. 3,899, the sport being further treated by the process set forth in U.S. Pat. No. 4,724,276, so as to impart self-branching characteristics thereto.

Classification:

*Botanic.*—*Euphorbia pulcherrima* Willd.

*Common name.*—Poinsettia.

*Cultivar name.*—'135'.

Form: Shrub.

Height: Medium.

Growth habit: As a single stemmed plant, upright and vigorous. In full flower, the stem is terminated by a large inflorescence, with several smaller flowering side shoots lower on the stem. Observations of 3 plants in a pot with an overall height of 43 cm. and an overall width of 50 cm. were made. The bract diameter of individual flowers was 33 cm.

Branching: Branching can be enhanced by removal of the stem tip. Then, several flowering branches with equal vigor may develop on a single plant.

Growth Rate: Very fast. Rooting of stem cuttings occurs in 12–18 days under intermittent mist. The plant will flower in about ten weeks under continuous long night conditions and night temperatures of about 16–18 degrees C.

Foliage: The foliage is clean and uniformly green from bottom to top of the plant. The leaves are of medium size, leaf blades typically being about 14–16 cm. long and about 8–10 cm. wide with leaf petioles about 6–7 cm. long.

Leaf shape: Typical leaves are ovate with obtuse bases and acuminate tips. Leaf margins are mostly entire with slight lobing and minor indentations on each side of the blade.

Color:

*Upper side.*—Darker than R.H.S. 147B, lighter than R.H.S. 147A.

*Under side.*—Near R.H.S. 137C.

Retention: The foliage retention is good even under low light intensities in the consumer's home.

Bracts: Generally there are 21–24 bicolored red and white bracts of various sizes subtending the cyathia. The primary bracts have blades typically 14–16 cm. long and 8–10 cm. wide with petioles about 3 cm. long.

Shape: Bracts are mostly ovate with acute bases and acuminate tips. Primary bracts are mostly entire with some slight lobing.

Color:

*Upper side.*—Bicolored: White bracts with red splotches. White background near R.H.S. 155A. Red splotches between R.H.S. 53B and 53C.

*Under side.*—Bicolored: White near R.H.S. 155A. Red near R.H.S. 53C.

Cyathia: Generally, 15–18 cyathia (flowers) develop when the plant is in "full bloom". Each cyathium is about 6–7 mm long and about 5–6 mm wide, green in color, and fringed with yellow at the distal end. Usually, only one bright yellow nectar cup protrudes from the side of each cyathium. The flower pedicel is also green and about 5–6 mm in length. The anthers protruding from the cyathia are white.

What is claimed:

1. A new and distinct Poinsettia cultivar, substantially as herein shown and described, distinguished by its predominantly white bracts bearing scattered red splotches, stiff-stemmed, and vigorous growth habits.

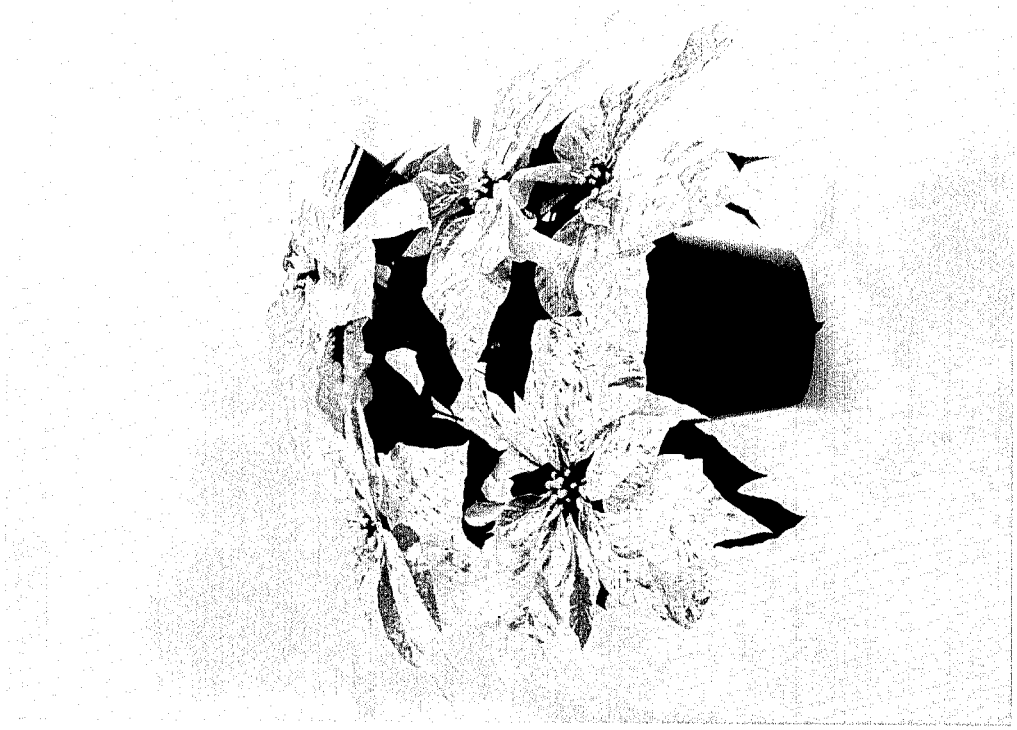
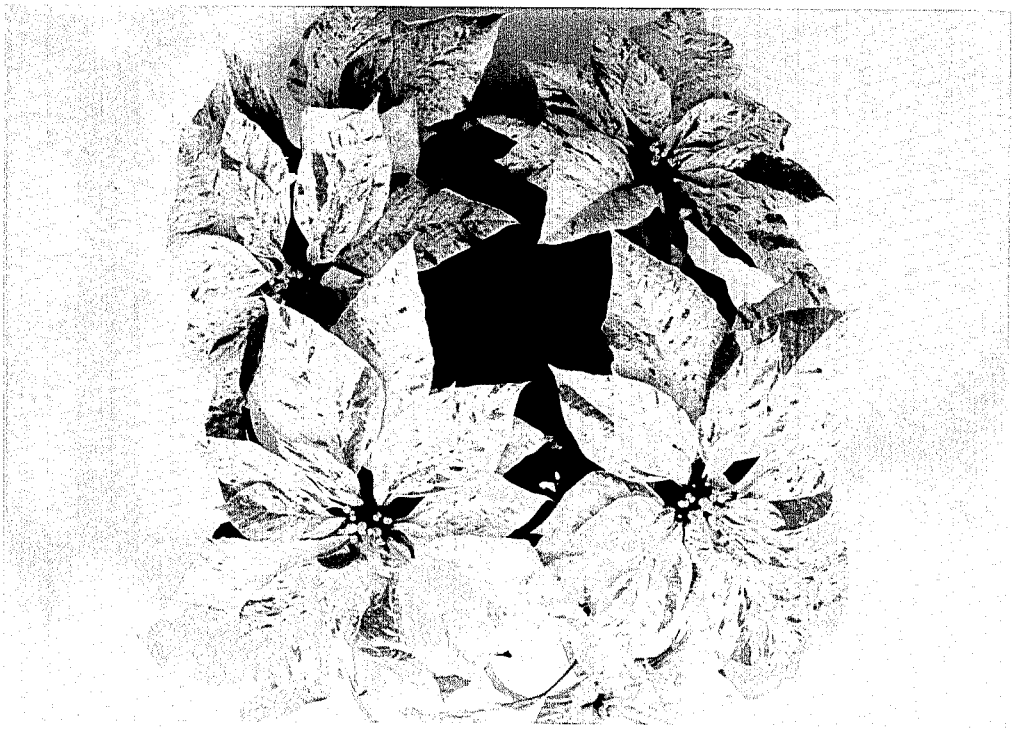

* * * * *